US008845667B2

(12) United States Patent
Cruz Hernandez et al.

(10) Patent No.: US 8,845,667 B2
(45) Date of Patent: Sep. 30, 2014

(54) SURGICAL TOOL HAVING A PROGRAMMABLE ROTARY MODULE FOR PROVIDING HAPTIC FEEDBACK

(75) Inventors: Juan Manuel Cruz Hernandez, Montreal (CA); Andrew Gosline, Montreal (CA); Christopher Ullrich, Ventura, CA (US)

(73) Assignee: Immersion Corporation, San Jose, CA (US)

( * ) Notice: Subject to any disclaimer, the term of this patent is extended or adjusted under 35 U.S.C. 154(b) by 371 days.

(21) Appl. No.: 13/185,438

(22) Filed: Jul. 18, 2011

(65) Prior Publication Data

US 2013/0023917 A1 Jan. 24, 2013

(51) Int. Cl.
| | |
|---|---|
| *A61B 17/32* | (2006.01) |
| *A61B 17/28* | (2006.01) |
| *A61B 17/3201* | (2006.01) |
| *A61B 19/00* | (2006.01) |
| *A61B 17/00* | (2006.01) |

(52) U.S. Cl.
CPC ......... *A61B 17/28* (2013.01); *A61B 2019/2292* (2013.01); *A61B 2017/00402* (2013.01); *A61B 2017/00398* (2013.01); *A61B 2019/465* (2013.01); *A61B 17/3201* (2013.01); *A61B 17/2816* (2013.01); *A61B 2017/00871* (2013.01); *A61B 2019/467* (2013.01)
USPC .......................................... 606/174; 606/208

(58) Field of Classification Search
CPC ........... A61B 2017/00402; A61B 2017/00871; A61B 2017/00398; A61B 17/3201; A61B 17/2816; A61B 17/28; A61B 2019/467; A61B 2019/465; A61B 2019/2292
USPC ............. 345/156; 606/174, 208; 30/179, 192, 30/223, 227, 246, 263
See application file for complete search history.

(56) References Cited

U.S. PATENT DOCUMENTS

| | | | |
|---|---|---|---|
| 3,785,381 | A | 1/1974 | Lower et al. |
| 3,950,984 | A | 4/1976 | Russel |

(Continued)

FOREIGN PATENT DOCUMENTS

| | | |
|---|---|---|
| CA | 2520942 | 3/2007 |
| DE | 4213426 | 10/1992 |

(Continued)

OTHER PUBLICATIONS

EP Appl. No. 11 17 6993, Extended European Search Report, dated Nov. 8, 2011.

(Continued)

*Primary Examiner* — Thomas McEvoy
*Assistant Examiner* — Julie A Szpira
(74) *Attorney, Agent, or Firm* — Medler Ferro PLLC

(57) ABSTRACT

A surgical tool such as a grasper or a pair of surgical scissors includes a hinge portion that spans between a handle proximal portion and a distal working portion to communicate mechanical actions of the handle proximal portion to the distal working portion. A programmable rotary module is coupled to the hinge portion and includes a sensor, an actuator, and a controller. The sensor, actuator, and controller may be enclosed in a common housing. The sensor measures rotation of the distal working portion and the actuator generates haptic effects to the proximal handle portion. A controller is electrically connected to the sensor and to the actuator. The controller receives the rotation measurements from the sensor and, based upon the rotation measurements, outputs a control signal to the actuator relating to the generation of haptic effects. The haptic effects may include force sensations such as detents and barriers.

20 Claims, 6 Drawing Sheets

(56) References Cited

U.S. PATENT DOCUMENTS

| | | | |
|---|---|---|---|
| 4,407,686 A | 10/1983 | Cook et al. | |
| 4,608,861 A | 9/1986 | Wachtler et al. | |
| 4,841,987 A | 6/1989 | Brown et al. | |
| 4,858,611 A | 8/1989 | Elliott | |
| 5,047,046 A | 9/1991 | Bodoia | |
| 5,188,111 A | 2/1993 | Yates et al. | |
| 5,339,799 A | 8/1994 | Kami et al. | |
| 5,357,956 A | 10/1994 | Nardella | |
| 5,389,849 A | 2/1995 | Asano et al. | |
| 5,411,511 A | 5/1995 | Hall | |
| 5,503,320 A | 4/1996 | Webster et al. | |
| 5,529,235 A | 6/1996 | Boiarski et al. | |
| 5,609,607 A | 3/1997 | Hechtenberg et al. | |
| 5,623,582 A | 4/1997 | Rosenberg | |
| 5,649,934 A | 7/1997 | Smeltzer, III et al. | |
| 5,685,474 A | 11/1997 | Seeber | |
| 5,688,270 A | 11/1997 | Yates et al. | |
| 5,713,896 A * | 2/1998 | Nardella | 606/50 |
| 5,728,044 A | 3/1998 | Shan | |
| 5,733,281 A | 3/1998 | Nardella | |
| 5,767,840 A | 6/1998 | Selker | |
| 5,771,902 A | 6/1998 | Lee et al. | |
| 5,810,880 A | 9/1998 | Jensen et al. | |
| 5,833,634 A | 11/1998 | Laird et al. | |
| 5,836,894 A | 11/1998 | Sarvazyan | |
| 5,928,158 A | 7/1999 | Aristides | |
| 5,928,159 A | 7/1999 | Eggers et al. | |
| 5,950,629 A | 9/1999 | Taylor et al. | |
| 5,965,880 A | 10/1999 | Wolf et al. | |
| 5,989,199 A | 11/1999 | Cundari et al. | |
| 6,004,335 A | 12/1999 | Vaitekunas et al. | |
| 6,024,741 A | 2/2000 | Williamson et al. | |
| 6,063,031 A | 5/2000 | Cundari et al. | |
| 6,096,004 A | 8/2000 | Meglan et al. | |
| 6,132,441 A | 10/2000 | Grace | |
| 6,190,334 B1 | 2/2001 | Lasky et al. | |
| 6,267,761 B1 | 7/2001 | Ryan | |
| 6,354,147 B1 | 3/2002 | Gysling et al. | |
| 6,375,471 B1 | 4/2002 | Wendlant et al. | |
| 6,423,057 B1 | 7/2002 | He et al. | |
| 6,436,107 B1 | 8/2002 | Wang et al. | |
| 6,451,015 B1 | 9/2002 | Rittman, III et al. | |
| 6,494,882 B1 | 12/2002 | Lebouitz et al. | |
| 6,594,552 B1 | 7/2003 | Nowlin et al. | |
| 6,690,963 B2 | 2/2004 | Ben-Haim et al. | |
| 6,718,196 B1 | 4/2004 | Mah et al. | |
| 6,730,021 B2 | 5/2004 | Vassiliades, Jr. et al. | |
| 6,810,281 B2 | 10/2004 | Brock et al. | |
| 6,817,973 B2 | 11/2004 | Merril et al. | |
| 6,945,981 B2 | 9/2005 | Donofrio et al. | |
| 6,969,384 B2 | 11/2005 | de Juan, Jr. et al. | |
| 7,108,695 B2 | 9/2006 | Witt et al. | |
| 7,118,582 B1 | 10/2006 | Wang et al. | |
| 7,122,028 B2 | 10/2006 | Looper et al. | |
| 7,126,303 B2 | 10/2006 | Farritor et al. | |
| 7,200,445 B1 | 4/2007 | Dalbec et al. | |
| 7,206,627 B2 | 4/2007 | Abovitz et al. | |
| 7,270,664 B2 | 9/2007 | Johnson et al. | |
| 7,280,863 B2 | 10/2007 | Shachar | |
| 7,300,450 B2 | 11/2007 | Vleugels et al. | |
| 7,366,562 B2 | 4/2008 | Dukesherer et al. | |
| 7,373,219 B2 | 5/2008 | Nowlin et al. | |
| 7,393,354 B2 | 7/2008 | Buchman et al. | |
| 7,422,139 B2 | 9/2008 | Shelton, IV et al. | |
| 7,720,532 B2 | 5/2010 | Hashimshony et al. | |
| 7,771,424 B2 | 8/2010 | McGaffigan | |
| 7,963,192 B2 * | 6/2011 | Mayenberger et al. | 76/106.5 |
| 8,216,212 B2 * | 7/2012 | Grant et al. | 606/1 |
| 2001/0004700 A1 | 6/2001 | Honeycutt et al. | |
| 2001/0025150 A1 | 9/2001 | de Juan, Jr. et al. | |
| 2002/0112547 A1 | 8/2002 | Eltaib et al. | |
| 2002/0120188 A1 | 8/2002 | Brock et al. | |
| 2003/0023250 A1 | 1/2003 | Watschke et al. | |
| 2003/0057973 A1 | 3/2003 | Nojima et al. | |
| 2004/0009459 A1 | 1/2004 | Anderson et al. | |
| 2004/0019447 A1 | 1/2004 | Shachar | |
| 2004/0106916 A1 | 6/2004 | Quaid et al. | |
| 2004/0167559 A1 | 8/2004 | Taylor et al. | |
| 2004/0249268 A1 | 12/2004 | Da Silva | |
| 2005/0021024 A1 | 1/2005 | Hooven | |
| 2005/0090815 A1 | 4/2005 | Francischelli et al. | |
| 2005/0131390 A1 | 6/2005 | Heinrich et al. | |
| 2005/0223327 A1 | 10/2005 | Cunningham et al. | |
| 2005/0245910 A1 | 11/2005 | Wright et al. | |
| 2006/0030845 A1 | 2/2006 | Leung et al. | |
| 2006/0033703 A1 * | 2/2006 | Olien et al. | 345/156 |
| 2006/0095033 A1 | 5/2006 | Garabedian et al. | |
| 2006/0142657 A1 | 6/2006 | Quaid et al. | |
| 2006/0206031 A1 | 9/2006 | Hasegawa | |
| 2006/0207978 A1 | 9/2006 | Rizun et al. | |
| 2006/0264755 A1 | 11/2006 | Maltz et al. | |
| 2006/0278680 A1 | 12/2006 | Viola et al. | |
| 2006/0279534 A1 | 12/2006 | Powers et al. | |
| 2006/0293643 A1 | 12/2006 | Wallace et al. | |
| 2007/0043352 A1 | 2/2007 | Garrison et al. | |
| 2007/0062547 A1 | 3/2007 | Pappone | |
| 2007/0073282 A1 | 3/2007 | McGaffigan et al. | |
| 2007/0112284 A1 | 5/2007 | Hoffman et al. | |
| 2007/0135735 A1 | 6/2007 | Ellis et al. | |
| 2007/0142749 A1 | 6/2007 | Khatib et al. | |
| 2007/0175962 A1 | 8/2007 | Shelton, IV et al. | |
| 2007/0175964 A1 | 8/2007 | Shelton et al. | |
| 2007/0270884 A1 | 11/2007 | Smith et al. | |
| 2007/0279401 A1 | 12/2007 | Ramstein et al. | |
| 2008/0009747 A1 | 1/2008 | Saadat et al. | |
| 2008/0086120 A1 | 4/2008 | Mirza et al. | |
| 2008/0117166 A1 | 5/2008 | Rosenberg | |
| 2008/0161796 A1 | 7/2008 | Cao et al. | |
| 2008/0167662 A1 | 7/2008 | Kurtz | |
| 2008/0167672 A1 | 7/2008 | Giordano et al. | |
| 2008/0197167 A1 | 8/2008 | Viola et al. | |
| 2008/0251568 A1 | 10/2008 | Zemlok et al. | |
| 2008/0251569 A1 | 10/2008 | Smith et al. | |
| 2009/0090763 A1 | 4/2009 | Zemlok et al. | |
| 2009/0163904 A1 | 6/2009 | Miller et al. | |
| 2010/0179423 A1 * | 7/2010 | Ramstein et al. | 600/437 |
| 2011/0046659 A1 | 2/2011 | Ramstein et al. | |
| 2011/0062211 A1 * | 3/2011 | Ross et al. | 227/175.1 |
| 2011/0118779 A1 * | 5/2011 | Olien et al. | 606/205 |
| 2011/0288573 A1 | 11/2011 | Yates et al. | |
| 2012/0041436 A1 | 2/2012 | Ullrich et al. | |
| 2012/0138658 A1 | 6/2012 | Ullrich et al. | |
| 2012/0143182 A1 | 6/2012 | Ullrich | |

FOREIGN PATENT DOCUMENTS

| | | |
|---|---|---|
| EP | 1 254 637 | 11/2002 |
| EP | 2 044 890 | 4/2009 |
| EP | 2 218 409 | 8/2010 |
| EP | 2 277 458 | 1/2011 |
| EP | 2 283 781 | 2/2011 |
| EP | 2 417 925 | 2/2012 |
| JP | 5-38327 A | 2/1993 |
| WO | WO 94/24949 | 11/1994 |
| WO | WO 03/020139 | 3/2003 |
| WO | WO 03/090630 | 11/2003 |
| WO | WO 2004/067053 | 8/2004 |
| WO | WO 2005/013803 | 2/2005 |
| WO | WO 2005/110304 | 11/2005 |
| WO | 2007/067628 | 6/2007 |
| WO | WO 2008/033937 | 3/2008 |
| WO | WO-2009/009220 A2 | 1/2009 |
| WO | WO-2010/008663 A1 | 1/2010 |
| WO | WO-2010/065314 A1 | 6/2010 |
| WO | WO-2010/083060 A1 | 7/2010 |

OTHER PUBLICATIONS

EP Appl. No. 11 19 1549, Extended European Search Report, dated Feb. 22, 2012.

(56) References Cited

OTHER PUBLICATIONS

"Tactile Sensor Acts as a Human Finger in Minimally Invasive Surgery", www.physorg.com/news102155952.html, 2007.
Bethea, et al., Abstract of: "Application of Haptic Feedback to Robotic Surgery", http://www.liebertonline.com/doi/abs/10.1089/1092642041255441, Downloaded: Nov. 25, 2008.
Bholat, et al., Abstract of: "Tactile Feedback is Present During Minimally Invasive Surgery", J Am Coil Surg, Oct. 1999, 189(4), pp. 349-355; http://www.ncbi.nlm.nih.gov/pubmed/10509459, Downloaded: Nov. 25, 2008.
Hannaford, et al., "Computerized Endoscopic Surgical Grasper", Proceedings, Medicine Meets Virtual Reality, San Diego, CA, Jan. 1998.
Hu, et al., "Real-Time Haptic Feedback in Laparoscopic Tools for Use in Gastro-Intestinal Surgery", T. Dohi and R. Kikinis (Eds.): MICCAI 2002, LNCS 2488, (2002), pp. 66-74.
Marvik, et al., Abstract of: "Ergonomic Design Criteria for a Novel Laparoscopic Tool Handle with Tactile Feedback", Minerva Chirurgica ISSN 0026-4733, vol. 61, No. 5, (2006), pp. 435-444.
Moy, et al., Abstract of: "A Compliant Tactile Display for Teletaction", http://ieeexplore.ieee.org/xpl/freeabs_all.jsp?tp=&arnumber=845247&isnumber=18314, Downloaded: Nov. 25, 2008.
Okamura, et al., "The Haptic Scissors: Cutting in Virtual Environments", Proceedings of the 2003 IEEE International Conference on Robotics & Automation, Taipei, Taiwan, Sep. 14-19, 2003.
Schirmbeck, et al., "Tactile Feedback without Direct Touch: An Achievement for Robotically Working Heart Surgeons?", nereja.free.fr/files/BMT2005Haptic1.pdf, Downloaded: Nov. 25, 2008.
Yao, et al., "A Tactile Enhancement Instrument for Minimally Invasive Surgery", Computer Aided Surgery, vol. 10, No. 4, pp. 233-239, MICCAI (2004), pp. 89-96.
International Search Report for PCT/US2012/047006, (Oct. 5, 2012).

\* cited by examiner

US 8,845,667 B2

SURGICAL TOOL HAVING A PROGRAMMABLE ROTARY MODULE FOR PROVIDING HAPTIC FEEDBACK

FIELD OF THE INVENTION

The invention relates to a surgical tool having a programmable rotary module for providing haptic feedback to the operator, the feedback relating to rotation of a portion of the surgical tool.

BACKGROUND OF THE INVENTION

As opposed to open surgery in which a surgeon cuts a relatively large incision in the skin of a patient for accessing internal organs, minimally invasive surgical procedures are performed by making relatively small incisions and then inserting tools through the incisions to access the organs. Minimally invasive surgery usually results in shorter hospitalization times, reduced therapy requirements, less pain, less scarring, and fewer complications.

Although minimally invasive surgical procedures involving small incisions include many advantages over open surgery, minimally invasive surgery can still create challenges to a surgeon. For example, the surgeon must typically rely on a miniature camera introduced through an incision to view the patient's internal organs and see how the movement and operation of the tools affects the organs. The camera transmits images to a visual display, allowing the surgeon to see the internal organs and tissues and to see the effect of other minimally invasive tools on the organs and tissues. In this way, the surgeon is able to perform laparoscopic surgery, dissection, cauterization, endoscopy, telesurgery, and the like. Compared to open surgery, however, minimally invasive surgery can present limitations regarding the surgeon's ability to see and feel the patient's organs and tissues. In laparoscopic surgery, surgeons have limited capacity to palpate or manipulate tissues to enable procedural progress. In some cases, this can result in converting the procedure from closed to open to facilitate identification of various structures or management of operative complications.

Many existing laparascopic hand tools make extensive use of complex mechanical assemblies to indicate the status of the tool for correct use and reinforce the importance of correct use to the operator. However, such mechanical assemblies may be complex, bulky, and/or costly to incorporate into the surgical tools. It is an object hereof to provide effective haptic effects to a user operated surgical tool via a programmable haptic device that allows generation and delivery of a force feedback effect to a user.

BRIEF SUMMARY OF THE INVENTION

The invention is a surgical tool comprising a hinge portion that spans between a handle proximal portion and a distal working portion. The hinge portion communicates mechanical actions of the handle proximal portion to the distal working portion. A programmable rotary module is coupled to the hinge portion and includes a sensor, an actuator, and a controller. The sensor measures rotation of the distal working portion and the actuator generates haptic effects to the proximal handle portion. A controller is electrically connected to the sensor and to the actuator. The controller receives the rotation measurements from the sensor and, based upon the rotation measurements, outputs a control signal to the actuator relating to the generation of haptic effects.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
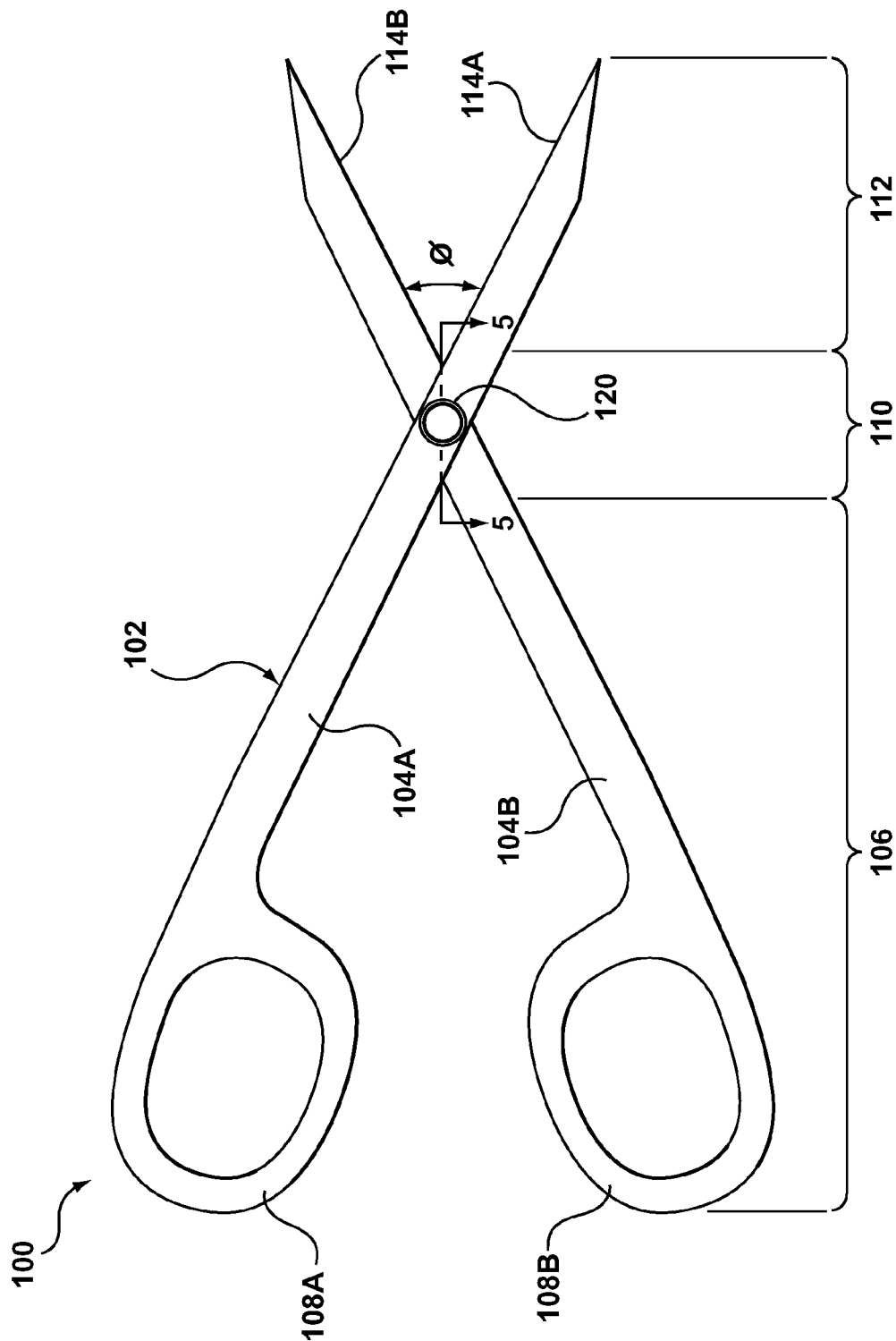
FIG. 1 is a top view schematic of a surgical tool according to an embodiment hereof, wherein the surgical tool has a programmable rotary module coupled thereto for providing haptic effects.

FIG. 1 illustrates a surgical tool 100 having a programmable rotary module 120 coupled thereto for providing haptic effects relating to the operator to indicate the status of surgical tool 100. In the embodiment of FIG. 1, surgical tool 100 is a pair of surgical scissors having a first arm 104A and a second arm 104B that cross or overlap each other at a hinge portion 110. Hinge portion 110 spans between a handle proximal portion 106 and a distal working portion 112 and communicates mechanical actions of handle proximal portion 106 to distal working portion 112. More particularly, the motion of handle proximal portion 106 enlarges or reduces the angle Ø between arms 104A, 104B along the distal working portion 112. In other words, handle proximal portion 106 opens and closes distal working portion 112. Arms 104A, 104B include finger-receiving portions 108A, 108B, respectively, on handle portion 106, and include distal tips 114A, 114B, respectively, on working portion 112. When surgical tool 100 is a pair of surgical scissors as shown, distal tips 114A, 114B include cutting blades. However, it should be understood that distal tips 114A, 114B may include any suitable structure depending on the functionality of surgical tool 100. Laparoscopic tools in general, like tool 100, are typically thin instruments that each have varied functions and that can be introduced by the surgeon into the abdomen or other areas of the body through trocars, which are hollow tubes with a rubber seal to keep CO$_2$ from leaking. Surgical tool 100 is not limited to surgical scissors, but may be any surgical tool having two or more distal arms rotatable with respect to each other such as but not limited to a gripper/grasper, separator, clamp, or manipulator. In addition, it is not required that surgical tool 100 be a laparoscopic hand tool.

Figure 2:
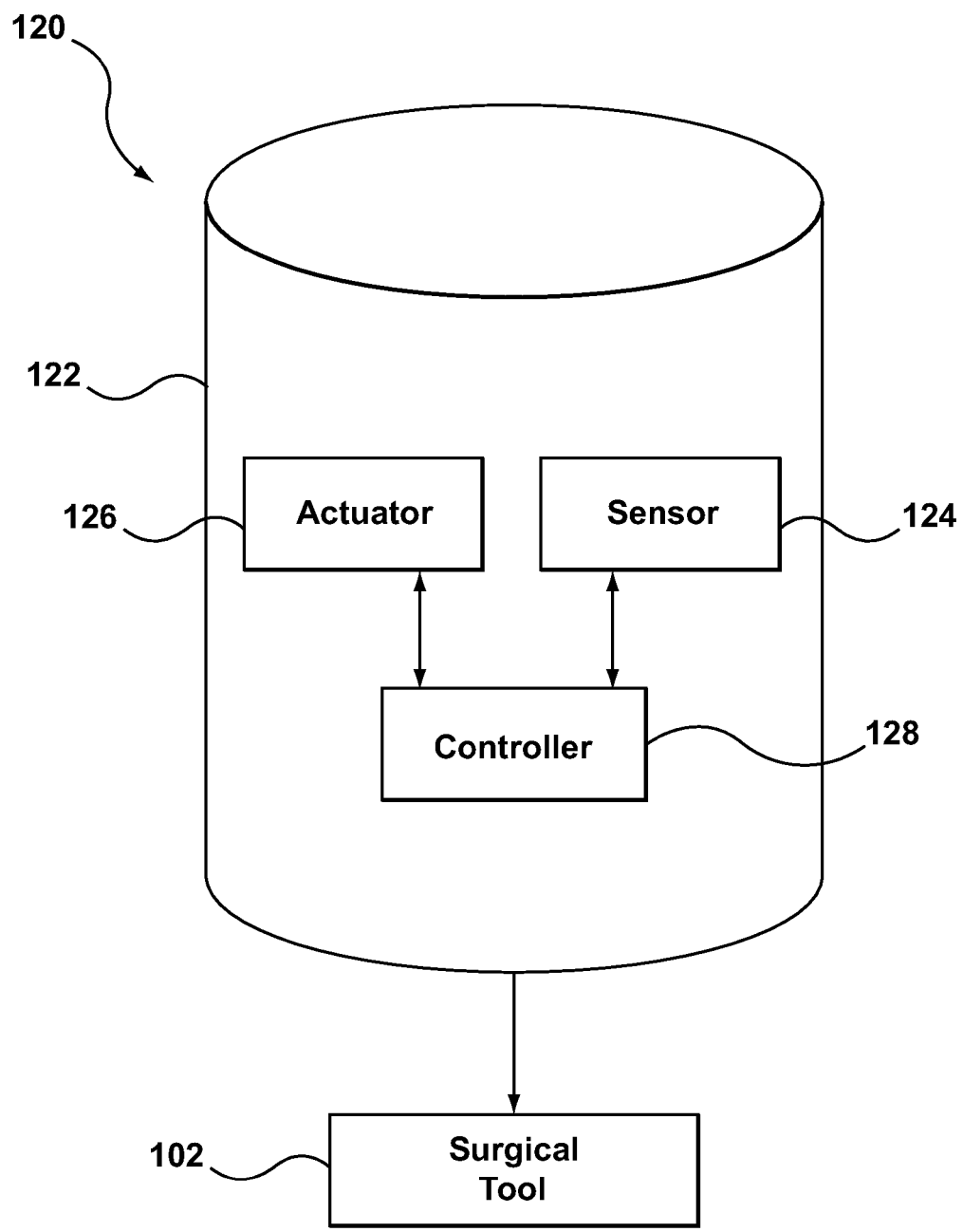
FIG. 2 illustrates a block diagram of the programmable rotary module of FIG. 1 according to an embodiment hereof.

Programmable rotary module 120 is coupled to hinge portion 110 of surgical tool 100. As surgical tool 100 is operated, rotary module 120 measures rotation or angular movement of a portion of surgical tool 100 and generates haptic effects to a proximal or handle portion 106 of surgical tool 100. FIG. 2 illustrates a block diagram of programmable rotary module 120 according to an embodiment hereof. Programmable rotary module 120 includes a housing 122 that contains one or more sensors 124, one or more actuators 126, and a controller 128. In one embodiment, programmable rotary module 120 may be a PR-1000, PR-3000, or PR-5000 TouchSense® Module available from Immersion Corporation of San Jose, Calif. However, other appropriate programmable rotary modules may be used with surgical tool 100 and is not limited to the device described herein. One or more sensors 124 are electrically connected to controller 128 such that one or more sensors 124 measure and encode the rotary position, velocity, acceleration, linear force and/or torque information of programmable rotary module 120 to controller 128. One or more actuators 126 are electrically connected to controller 128 and controller 128 communicates the information received from sensor 124 to actuator 126. One or more actuators 126 output haptic effects to surgical tool 100 upon receiving an appropriate haptic signal from the controller 128. Such haptic effects include, but are not limited to, detents, barriers or hard stops, and/or kinesthetic feedback (e.g., active and resistive force feedback). A power supply (not shown) can be coupled to actuator 126, controller 128, or any other components as required to provide electrical power. Power can also be stored and regulated by controller 128 and thus used when needed to drive actuator 128.

Sensor 124 may be one of several commercially available input transducers. Input transducers suitable for use as sensor 124 of programmable rotary module 120 include but are not limited to an encoded wheel transducer, an optical encoder, a Hall effect sensor, a potentiometer and electroactive polymers. Sensor 124 measures rotation of a portion of surgical tool 100 by sensing one or more of the rotary position of the proximal handle portion, the velocity at which the proximal handle portion is rotated, the acceleration at which the proximal handle portion is rotated, the linear force applied to the proximal handle portion, and/or the torque applied to the proximal handle portion. A sensor interface (not shown) may optionally be connected between sensor 124 and controller 128 to convert sensor signals to signals that can be interpreted by controller 128. For example, the sensor interface can receive signals from a digital sensor such as an encoder and convert the signals into a digital binary number. An analog to digital converter (ADC) can also be used. Such circuits, or equivalent circuits, are well known to those skilled in the art. Alternately, the sensor interface circuitry can be provided within controller 128 or in the sensor 124.

Actuator 126 may be one of several commercially available output transducers that are capable of producing electrically modulated forces to surgical tool 100 in response to signals output by controller 128 or other electronic logic or device, i.e., meaning that controller 128 or another electronic device controls application of the forces. In one embodiment, actuator 126 is a passive actuator capable of producing resistance, i.e., a braking force, to surgical tool 100 to simulate the resistance encountered during opening and/or closing of distal working portion 112. For example, actuator 126 may include pneumatic/hydraulic passive actuators, electromagnetic brakes, magnetic particle brakes, friction brakes, or magneto-rheologic or electro-rheologic brakes utilizing a magnetic core, a coil or a magnetic target. In another embodiment, actuator 126 may alternatively or additionally include an active actuator. Active actuators may be utilized to produce resistance or a braking force to surgical tool 100 to simulate the resistance encountered during opening and/or closing of distal working portion 112 and may also be utilized to provide active haptic effects to surgical tool 100, meaning that programmable rotary module 120 automatically controls distal working portion 112 of surgical tool 100. For example, programmable rotary module 120 may cause a specific amount of opening or closing of distal working portion 112 by actively supplying torque to hinge 110. Active output transducers suitable for use herein include but are not limited to stepper motors, servo motors, a torquer which is a motor with limited angular range, pneumatic/hydraulic active actuators, DC motors, ultrasonic motors, or electroactive polymers. A more detailed description of possibly haptic actuators suitable for use herein may be found in U.S. patent application Ser. No. 11/862,639, filed Sep. 28, 2007, herein incorporated by reference in its entirety. An actuator interface (not shown) can be optionally connected between actuator 126 and controller 128 to convert signals from controller 128 into signals appropriate to drive the actuators. The actuator interface can include power amplifiers, switches, digital to analog controllers (DACs), and other components, as well known to those skilled in the art. Alternately, the actuator interface circuitry can be provided within controller 128 or in the actuator 126.

Controller 128 controls the application of the programmable haptic effects. In particular, controller 128 receives sensor information from sensor 124 and outputs signals to the programmable rotary module 120 to output selected haptic effects to the user based on the sensed position and instructions from controller 128. In one embodiment, controller 128, sensor 124, and actuator 126 are located within a common housing that is coupled to hinge 110 of surgical tool 100. Controller 128 is mounted within or on rotary programmable module 120 and one or more internal wires extend within the housing of rotary programmable module 120 to electrically connect controller 128 to sensor 124. In another embodiment however, one or more of the components of programmable rotary module 120 may be remotely located from hinge 110 of surgical tool 100. For example, controller 128 may be an external component or separated from programmable rotary module 120 that is electrically connected to sensor 124 and actuator 126 via internal or external wires. Further, sensor 124 and/or actuator 126 may also be remotely located from hinge 110 of surgical tool 100 with the sensed angular movement and force, respectively, being transmitted from or to hinge 110 of surgical tool 100 via one or more belts, wires, or other transmission systems. In such an embodiment, all three main parts of the programmable rotary module are non collocated. As will be understood by those of ordinary skill in the art, various combinations of collocated and non collocated parts are possible, such as for example, the sensor being coupled to the hinge of the tool with a remotely located actuator transmitting actuation forces through a belt or other transmission system.

Controller 128 may be a general-purpose or specific-purpose processing device or microcontroller for processing signals detected by sensor 124. Controller 128 can include one microprocessor chip, or multiple processors and/or co-processor chips, and can include digital signal processor (DSP) functionality. In one embodiment, controller 128 can be mounted on a printed circuit board, which includes circuitry for electrically coupling controller 128 to sensor 124 and actuator 126. The circuitry on the printed circuit board may include any suitable amplification and attenuation type circuitry, power sources for providing and regulating power to each component of programmable rotary module 120, and other circuitry for proper operation of controller 128. In one embodiment, logical instructions, commands, and/or code can be implemented in hardware and incorporated in controller 128 using discrete logic circuitry, an application specific integrated circuit ("ASIC"), a programmable gate array ("PGA"), a field programmable gate array ("FPGA"), etc., or any combination thereof. In another embodiment, controller 128 may be associated with a memory device (not shown) for storing data and/or instructions. The memory device can be any type of storage device or computer-readable medium, such as random access memory ("RAM") or read-only memory ("ROM"). The memory device stores logical instructions, commands, and/or code executed by controller 128. The memory device may also be located internal to controller 128, or any combination of internal and external memory. In another embodiment, logical instructions, commands, and/or code can be implemented in both hardware in controller 128 and software/firmware stored in the memory.

In one embodiment, controller 128 looks up the aspect of user manipulation in a table stored in a memory and outputs a haptic signal to actuator 126. In an embodiment, controller 128 uses algorithms or a combination of algorithms as well as look-up tables stored in a memory to generate the haptic signal. Programmable rotary module 120 is thus able to output a haptic effect which corresponds to the specific position of arms 104A, 104B within the distal working portion 112 of surgical tool 100. For example, programmable rotary module 120 outputs resistive or active feedback which increases the amount of force required, even to a value of infinity, by the user to move handle portion 106 of surgical tool 100. Programmable friction or damping effects may be used to augment or reduce ease of movement of hinge portion 110. Such haptic effects are "passive," meaning that programmable rotary module 120 effectively outputs haptic or kinesthetic cues or warnings as feedback to the user relating to the control of surgical tool 100. In another embodiment, the haptic effect may be "active," meaning that programmable rotary module 120 automatically controls distal working portion 112 of surgical tool 100. For example, programmable rotary module 120 may cause a specific amount of opening or closing of distal working portion 112 by actively supplying torque to hinge 110. In yet another embodiment, the haptic effects may be "hybrid," meaning a combination of both passive and active actuators are utilized for providing feedback to the user.

Figure 3:
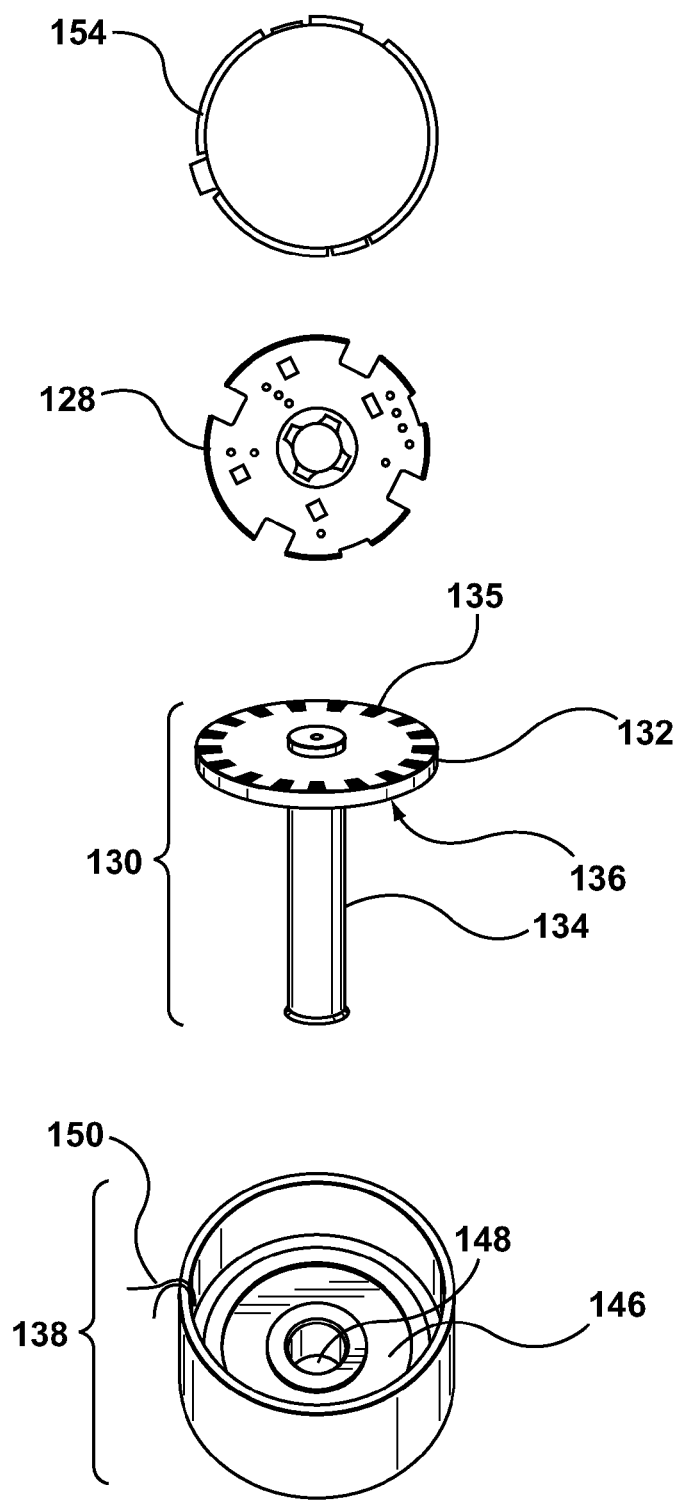
FIG. 3 is an exploded view schematic of a programmable rotary module of FIG. 2 according to an embodiment hereof.
Figure 4:
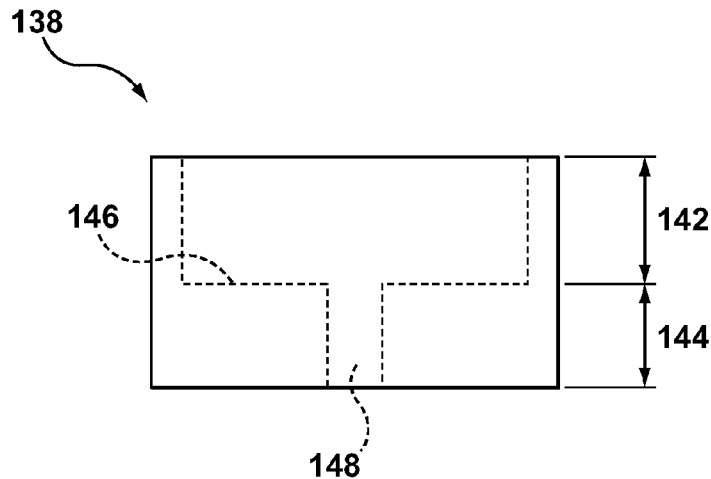
FIG. 4 is a side view schematic of a base unit of the programmable rotary module of FIG. 3.
Figure 5:
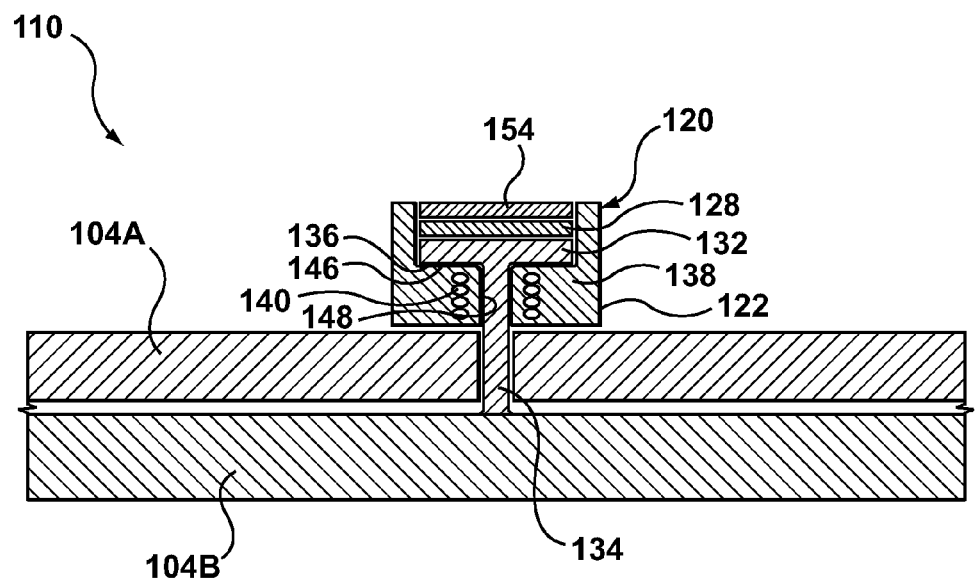
FIG. 5 is a sectional view of the programmable rotary module of FIG. 3 coupled to a hinge portion of the surgical tool of FIG. 1, taken along line 5-5 of FIG. 1.

One particular configuration of programmable rotary module 120 is shown in FIGS. 3, 4, and 5. In the embodiment of FIGS. 3, 4, and 5, programmable rotary module 120 includes a base unit 138, a rotatable insert 130, controller 128, and a cap 154. Referring to the exploded view of FIG. 3 and the side view of FIG. 4 as well, base unit 138 has a cylindrical outer shell that forms housing 122 of programmable rotary module. Base unit 138 includes a lower portion 144 and an upper portion 142. Lower portion 144 encloses a coil or encoder 140 (shown in the sectional view of FIG. 5), has a magnetic surface 146 formed thereon, and has a central passageway 148 extending therethrough. Upper portion 142 is hollow and forms a receptacle for receiving insert 130, controller 128, and cap 154. In particular, rotatable insert 130 includes a circular plate or disc 132 and a cylindrical rod or shaft 134 extending from an end surface 136 of plate 132. The exposed portion of surface 136, i.e., the portion of the surface not covered by shaft 134, has magnets or a magnetic material coupled thereto. An opposing end surface 135 of disc 132 includes a black and white pattern of hash marks 135 which serves as the scale or measure of angular rotation for sensor 124. When programmable rotary module 120 is assembled as shown in FIG. 5, shaft 134 of rotatable insert 130 is slidingly received through passageway 148 of base insert 138 and magnetic surface 136 of rotatable insert 130 faces and abuts against magnetic surface 146 of base unit 138. Rotatable insert 130 freely rotates within base insert 138. Controller 128 is placed on top of plate 132 and connected to coil 140 via internal wires 150. To finish assembly, cap 154 is placed on top of controller 128 to enclose and protect all the components within housing 122.

The sectional view of FIG. 5 illustrates how programmable rotary module 120 is coupled to hinge portion 110 of surgical tool 100. More particularly, shaft 134 of rotatable insert 130 extends through central passageway 148 of base unit 138 and through arm 104A of surgical tool 100 such that an end or bottom surface of shaft 134 may be coupled to arm 104B of surgical tool 100. Shaft 134 may be coupled to arm 104B in any suitable mechanical method, including but not limited to via adhesive, welding, or soldering. A bottom or end surface of base unit 138 is coupled to arm 104A of surgical tool in any suitable manner. As such, rotatable insert 130 rotates within base unit 138 as arms 104A, 104B rotate or angularly move with respect to each other. Coil 140 senses the relative rotary position of or movement between rotatable insert 130 and base unit 138 via magnetic surfaces 136, 146, respectively, which face and abut against each other as described above and utilizes the back and white pattern of hash marks 135 on rotatable insert 130 to measure the amount of rotation of hinge portion 100. The rotary position information is transmitted from coil 140 to emitter/receiver of sensor 124 on the embedded controller 128 via internal wires 150 and based on the sensed information, controller 128 outputs control signals to initiate selected haptic effects. Coil 140 and abutting magnetic surfaces 136, 146 also serve as a braking actuator that dissipates energy and resist user motion to output the selected haptic effects. Thus, in this embodiment, coil 140 and abutting magnetic surfaces 136, 146 serve as both the sensor and the actuator of programmable rotary module 120 and may be considered hybrid or bi-directional transducers in that the input and output transducers are paired together. As explained in more detail herein with respect to FIGS. 6A-6E, tactile effect parameters include the shape, width, amplitude, and number of detents, as well as the type and strength of bounding conditions in a barrier. A braking-based system affects a steeply sided detent having a saw-tooth or triangular shape with a sharp peak by applying the brake with increasing force. As arms 104A, 104B of surgical tool 100 continue to turn in relation to each other, the braking actuator lets go, applying zero force which gives the sensation of falling into the detent. A braking-based system affects a barrier by applying the brake, which sharply stops any further rotation in that direction.

More particularly, FIGS. 6A-6E illustrate examples of programmable haptic effect profiles useable with one or more embodiments described herein. In FIGS. 6A-6E, programmable rotary module 120 is shown on the right along with a representation of the haptic effect profile corresponding to programmable rotary module 120 shown on the left. It should be noted that the following haptic effect profiles are merely examples and that programmable rotary module 120 may be configured to output other haptic effect profiles not specifically described. It should be noted that programmable rotary module 120 may output a combination of two or more of the haptic effect profiles based on the application. In one embodiment, the haptic feedback according to one or more of the haptic effect profiles may be provided to the operator in a continuous manner as the operator performs the surgery. In another embodiment, feedback may be provided to the operator as an alert to notify or warn the operator when a particular condition is satisfied. Further, one type of feedback may be provided in a continuous manner while another type of feedback is provided as an alert. For example, detents may be provided/utilized in a continuous manner as the surgical tool is being opened or closed and barriers may be provided/utilized as an alert when the surgical tool is opened or closed to a particular angle.

Figure 6A:
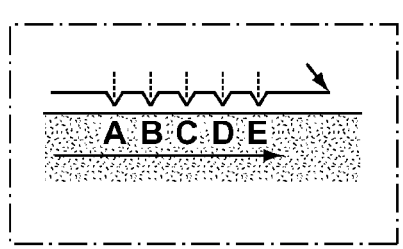
FIGS. 6A-6E are schematic illustrations of programmable haptic effect profiles useable with one or more embodiments hereof.
Figure 6A:
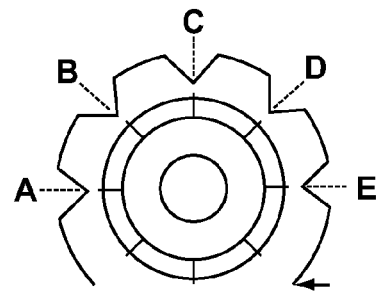

The force feedback output by programmable rotary module 120 may include a variety of different force sensations. The force feedback can be integrally implemented with the control functions performed by programmable rotary module 120. FIG. 6A depicts a programmable detent effect in accordance with an embodiment. A force detent is a force sensation that is output at particular rotational positions of surgical tool 100 to inform the user how much distal working portion 112 has rotated and/or to designate a particular position of programmable rotary module 120. The force detents can be simple jolts or bump forces to indicate the detent's position, or the detents can include forces that attract programmable rotary module 120 to the particular rotational detent position and resist movement of programmable rotary module 120 away from that position. Force feedback "snap-to" detents can also be provided, where a small force biases programmable rotary module 120 to the detent position when it is just outside the position. As shown in FIG. 6A, programmable detents A-E may emulate the feel and function of detents. Programmable detents may be added to complement existing mechanical detents or to further sub-divide existing mechanically-based detents. The magnitude, width, or overall feel of the resistive force applied by programmable rotary module 120 at each electronic-based detent may be programmed to be substantially similar to the force applied to surgical tool 100. FIG. 6C depicts a programmable hill effect profile. A hill is a plateau style of wide detent.

Also, the magnitude of the force detents can differ based on the value being controlled. For example, a particular higher angle Ø between arms 104A, 104B might be associated with a stronger force detent, while a lower angle Ø between arms 104A, 104B might be associated with a weaker force detent, thus informing the user generally of angle Ø between arms 104A, 104B without requiring the user to look at a visual display. This is particularly useful when the distal working portion 112 of surgical tool 100 is obscured from view during operation of surgical tool 100. In some embodiments, the user can also change the magnitude of detents associated with particular values to preferred values so as to "mark" favorite settings. Also, different sets of detent force profiles can be stored on controller 128 of programmable rotary module 120.

Figure 6B:
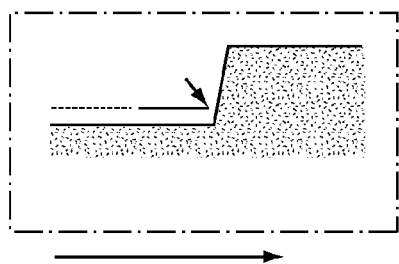
Figure 6B:
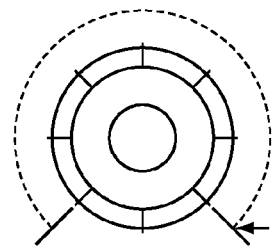
Figure 6C:
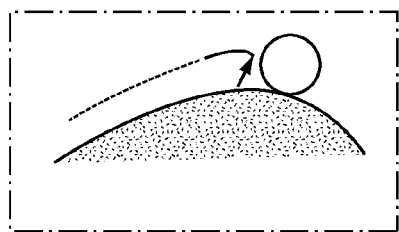
Figure 6C:
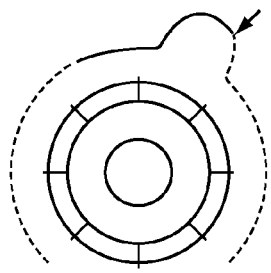

FIG. 6B depicts a programmable barrier or hard stop force effect profile in which the actuator is controlled to output an obstruction force to prevent or hinder the user from rotating arms 104A, 104B further in that direction. A barrier is particularly useful to prevent arms 104A, 104B from being opened or closed beyond a particular angle and thereby prevent unintentional injury to a patient. Programmable barriers may be used to emulate the feel and function of mechanical hard stops, and may be selectively output by programmable rotary module 120 based on the application of programmable rotary module 120.

Figure 6D:
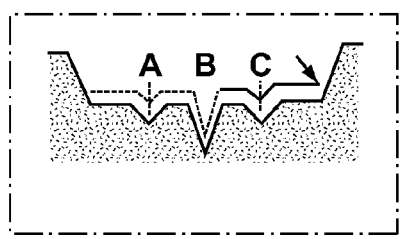
Figure 6D:
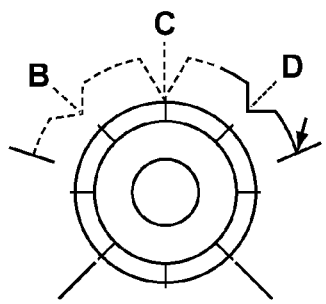

FIG. 6D depicts a programmable compound effect. A compound effect includes two or more effects such as barriers and detents. Compound effects help designers to closely match tactile sensations to operational steps, which may enhance usability. For the example shown in FIG. 6D, the compound effect may include small detents (shown as "A" and "C") with a deeper center detent (shown as "B") and barriers on each end.

Figure 6E:
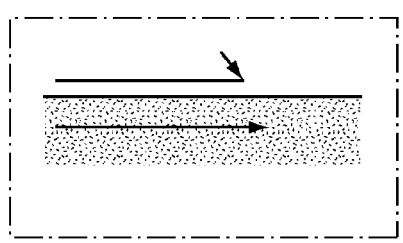
Figure 6E:
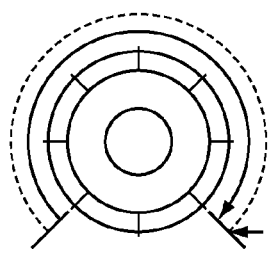

FIG. 6E depicts a constant force effect profile. A constant force effect is a continuous force independent of the instantaneous position of programmable rotary module 120. In other words, the force applied by the actuator does not necessarily change as programmable rotary module 120 is rotated toward or away from a certain position. However, the constant force effect may be activated and thus output by the actuator based on programmable rotary module 120 reaching a designated position. In addition, the constant force profile may be used to simulate dynamics such as gravity, friction or momentum. The controller sends a constant force output signal to the actuator when programmable rotary module 120 is sensed to be at a designated position.

Figure 7:
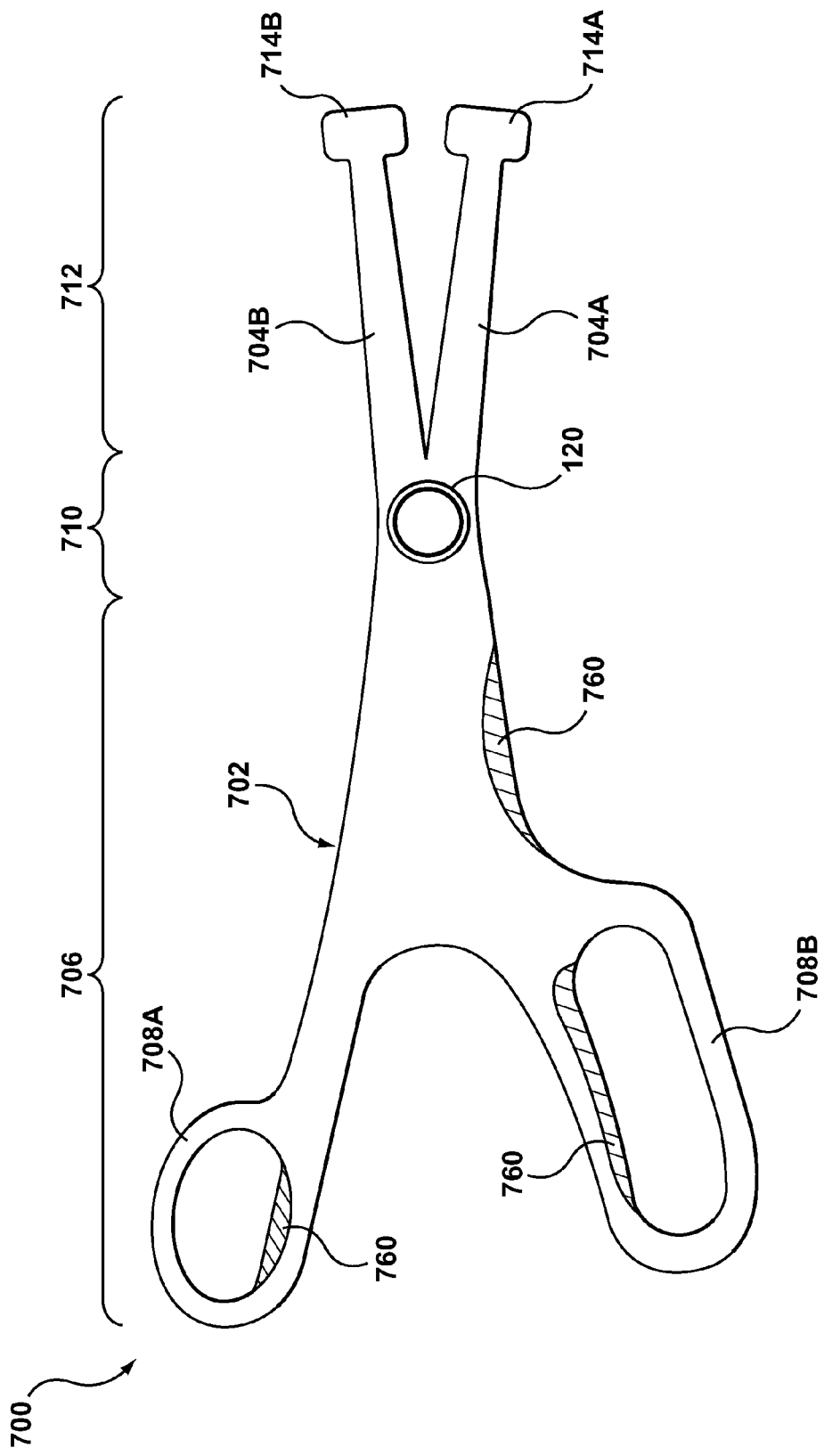
FIG. 7 is a top view schematic of a surgical tool according to another embodiment hereof, wherein the surgical tool has a programmable rotary module coupled thereto for providing haptic effects.

Referring to FIG. 7, another embodiment hereof is shown in which programmable rotary module 120 is coupled to a hinge portion 710 of a surgical tool 700. In the embodiment of FIG. 7, surgical tool 700 is a surgical grasper having a first arm 704A and a second arm 704B that cross or overlap each other at hinge portion 710. Hinge portion 710 spans between a handle proximal portion 706 and a distal working portion 712 and communicates mechanical actions of handle proximal portion 706 to distal working portion 712. More particularly, the motion of handle proximal portion 706 opens and closes distal working portion 712. Arms 704A, 704B include finger-receiving portions 708A, 708B, respectively, on handle portion 706, and include distal tips 714A, 714B, respectively, on working portion 712. In this embodiment, distal tips 714A, 714B include flat or planar surfaces suitable for gripping, grasping, separating, clamping, and/or manipulating tissue. Similar to the embodiment described above with respect to FIG. 1, rotary module 120 measures rotation or angular movement of a distal or working portion 712 of surgical tool 700 and generates haptic effects to a proximal or handle portion 706 of surgical tool 100. However, rather than the haptic effects being delivered only to the hinge portion of the surgical tool, surgical tool 700 also incorporates multiple haptic actuators in handle portion 706 at several locations 760 for providing haptic effects to the fingers and thumb of a hand of the surgeon. Haptic actuators 760 may include electromagnetic motors, eccentric rotating mass ("ERM") actuators in which an eccentric mass is moved by a motor, linear resonant actuators ("LRAs") in which a mass attached to a spring is driven back and forth, shape memory alloys, electro-active polymers that deform in response to signals, mechanisms for changing stiffness, vibrotactile actuators, inertial actuators, piezoelectric actuators, or other suitable types of actuating devices. A detailed description of possibly haptic actuators suitable for use herein may be found in U.S. patent application Ser. No. 11/862,639, filed Sep. 28, 2007, previously incorporated by reference in its entirety.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A surgical tool comprising:
   a handle proximal portion including a first arm and a second arm;
   a hinge portion between the handle proximal portion and a distal working portion, wherein the first arm and second arm overlap each other at the hinge portion and the hinge portion communicates mechanical actions of the handle proximal portion to the distal working portion;
   a programmable rotary module coupled to the hinge portion where the first arm and second arm overlap, the programmable rotary module including
      a sensor that measures rotation of the first arm and the second arm relative to each other,
      an actuator that generates haptic effects to the proximal handle portion, and
      a controller electrically connected to the sensor and electrically connected to the actuator, wherein the controller receives the rotation measurements from the sensor and, based upon the rotation measurements, outputs a control signal to the actuator relating to the generation of haptic effects.

2. The surgical tool of claim 1, wherein the sensor measures rotation of the first arm and the second arm relative to each other by sensing one or more of the rotary position of the first arm and the second arm relative to each other, the velocity at which the first arm and the second arm relative are rotated relative to each other, the acceleration at which the first arm and the second arm are rotated relative to each other, the linear force applied to the proximal handle portion, or the torque applied to the proximal handle portion.

3. The surgical tool of claim 1, wherein the haptic effects include detents.

4. The surgical tool of claim 1, wherein the haptic effects include barriers.

5. The surgical tool of claim 1, wherein the sensor, actuator, and controller are enclosed in a common housing.

6. The surgical tool of claim 1, wherein the distal working portion includes a pair of distal tips, wherein the distal tips are rotated relative to each other based on rotation of the first arm and the second arm.

7. The surgical tool of claim 6, wherein the distal tips include cutting blades.

8. The surgical tool of claim 6, wherein the distal tips include flat surfaces operable to grasp or grip tissue.

9. The surgical tool of claim 1, wherein the haptic effects are passive feedback cues.

10. The surgical tool of claim 1, wherein the haptic effects are active feedback that controls the distal working portion.

11. The surgical tool of claim 1, wherein the programmable rotary module includes a rotatable insert slidingly received within a passageway of a cylindrical base unit, wherein an encoder coil is housed within a portion of the base unit and operable to sense rotation between two abutting magnetic surfaces of the rotatable insert and the base unit.

12. The surgical tool of claim 11, wherein the rotatable insert includes a shaft coupled to the second arm and extending through the first arm and into the base unit coupled to the first arm such that the rotatable insert rotates within the base unit as the first and second arms open and close with respect to each other.

13. The surgical tool of claim 12, wherein the encoder and abutting magnetic surfaces also function as the actuator in a braking system.

14. The surgical tool of claim 1, further comprising a second haptic actuator embedded into the proximal handle portion that is electrically coupled to the programmable rotary module for providing additional haptic effects.

15. A surgical system comprising:
   a surgical tool including a first arm and a second arm that overlap at a hinge portion, wherein the hinge portion communicates mechanical actions of a handle proximal portion to a distal working portion;
   a programmable rotary module coupled to the surgical tool at the hinge portion, the programmable rotary module including
      a sensor that measures rotation of a portion of the surgical tool,
      an actuator that generates haptic effects to the proximal handle portion, and
      a controller electrically connected to the sensor and electrically connected to the actuator, wherein the controller receives the rotation measurements from the sensor and, based upon the rotation measurements, outputs a control signal to the actuator relating to the generation of haptic effects.

16. The surgical tool of claim 15, wherein the haptic effects include at least detents or barriers.

17. The surgical tool of claim 15, wherein the surgical tool is a grasper.

18. The surgical tool of claim 15, wherein the surgical tool is a pair of surgical scissors.

19. The surgical tool of claim 15, wherein the sensor, actuator, and controller are enclosed in a common housing and are coupled to the hinge portion of the surgical tool.

20. The surgical tool of claim 1, wherein the actuator is embedded into the proximal handle portion.

* * * * *